United States Patent [19]
Craig, Jr.

[11] Patent Number: 5,171,692
[45] Date of Patent: Dec. 15, 1992

[54] METHOD FOR DETECTING MERCURY AMALGAMATION OF ALUMINUM

[75] Inventor: Howard L. Craig, Jr., Mullica Hill, N.J.

[73] Assignee: Mobil Oil Corporation, Fairfax, Va.

[21] Appl. No.: 240,309

[22] Filed: Sep. 6, 1988

[51] Int. Cl.$^5$ ............................................. G01N 33/20
[52] U.S. Cl. ........................................ 436/73; 204/403
[58] Field of Search ............... 204/65, 98, 153.1, 197, 204/198, 222, 271, 287, 296, 292, 297 R, 402, 403, 404, 416, 430, 467, 435, 153.1; 324/444, 450; 429/27, 194, 112, 44; 436/73, 84; 422/53, 58, 22, 292

[56] References Cited

U.S. PATENT DOCUMENTS

| | | |
|---|---|---|
| 1,163,468 | 12/1915 | Schlumberger . |
| 1,163,469 | 12/1915 | Schlumberger . |
| 3,103,480 | 10/1963 | Watanabe et al. ............... 204/420 |
| 3,106,677 | 10/1963 | Edgar . |
| 3,134,071 | 5/1964 | Wakefield . |
| 3,293,155 | 12/1966 | Stone . |
| 3,549,993 | 12/1970 | Marsh et al. . |
| 3,565,769 | 2/1971 | Holden et al. ............... 204/153.1 |
| 3,887,399 | 6/1975 | Seiger ............................ 429/199 |
| 3,929,609 | 12/1975 | Gray et al. ..................... 204/405 |
| 3,964,982 | 6/1976 | Kim . |
| 3,975,681 | 8/1976 | Angelini et al. . |
| 3,999,121 | 12/1976 | Taylor, Jr. . |
| 4,006,063 | 2/1977 | Ensanian .................... 204/153.1 |
| 4,182,667 | 6/1980 | Dobson et al. ............... 204/153.1 |
| 4,191,920 | 3/1980 | Guttenplan et al. . |
| 4,278,519 | 7/1981 | Won . |
| 4,365,191 | 12/1982 | Weldon et al. . |
| 4,388,594 | 6/1983 | Deskins et al. . |
| 4,414,511 | 11/1983 | Waits et al. . |
| 4,455,212 | 6/1984 | Baxter ........................ 204/153.1 |
| 4,488,938 | 12/1984 | Jirovs Y et al. . |
| 4,584,530 | 4/1986 | Nicholson . |
| 4,758,324 | 7/1988 | Winneti et al. .................. 204/404 |

Primary Examiner—David L. Lacey
Assistant Examiner—Thomas E. Daley
Attorney, Agent, or Firm—Alexander J. McKillop; Charles J. Speciale

[57] ABSTRACT

A method for detecting mercury amalgamation of an aluminum body includes the steps of contacting a surface of the aluminum body with an electrolyte, and simultaneously contacting the electrolyte with a reference electrode. The reference electrode is formed of a metal which is more electronegative than the aluminum body being tested, such that the electrolyte creates an electrochemical cell between the aluminum and the reference electrode, which cell produces an electromotive potential between the aluminum and the reference electrode. The potential difference is monitored. The potential difference will differ when the aluminum surface contacted with the electrolyte is mercury amalgamated from when no mercury amalgamation is present in the aluminum surface contacted.

5 Claims, 2 Drawing Sheets

METHOD FOR DETECTING MERCURY AMALGAMATION OF ALUMINUM

BACKGROUND OF THE INVENTION

1. Field Of The Invention

This invention relates to a method and apparatus for detecting mercury amalgamation of aluminum, and more particularly relates to a method and apparatus for detecting the presence of mercury amalgams in the aluminum components of gas processing equipment.

2. Description of The Prior Art

The material of choice for heat exchangers in LNG and LPG plants is aluminum. Aluminum is chosen primarily because of its high thermal conductivity, ease of fabrication, reasonable cost and availability. A difficulty arising from the use of aluminum to construct heat exchangers for LNG plants is the fact that all natural gas contains measurable amount of mercury. Mercury is hazardous to aluminum equipment because the mercury promotes rapid deterioration of the aluminum once the mercury penetrates the coating of aluminum oxide usually present on aluminum surfaces. The aluminum becomes embrittled and is subject to failure when tensile stresses are applied.

In co-pending application, Ser. No. 093,277, filed on Sept. 4, 1987, now U.S. Pat. No. 4,380,829, which herein by reference, there is described a method for restoring the ductility of aluminum tubing whose metallurgical properties have been damaged by exposure to mercury. Thus, such a method relates to treating the aluminum body after the damage has occurred rather than detecting mercury amalgamation before the aluminum has deteriorated.

There are currently three ways of detecting mercury contamination of aluminum bodies when such contamination is suspected. Such conventional measures include visual observation on freely exposed surfaces, x-ray examination of hidden surfaces, as within crevices, and in the case of cracks, the use of conventional ultrasonic devices.

When visual observation is employed, the greatest reliance is placed on the sighting of aluminum corrosion product, variously termed, powder, whiskers, feathers or some similarly descriptive term for the crystals of beta-aluminum trihydrate, which is the characteristic result of moist air on amalgamated aluminum. However, the powder is so ephemeral and blows away so easily that it cannot be relied upon as a true indication of the site of the mercury corrosion attack.

X-rays have been used to locate incidental mercury liquid in the form of droplets, when such droplets are trapped in crevices, as in the space between a backing ring used to make a weld, and the weld itself. However, the sensitivity of x-rays towards amalgamated surfaces is not sufficiently high to detect mercury when it occurs in this form.

Ultrasonic devices have been employed to locate cracks caused by mercury, but such devices cannot discriminate between cracks caused by some other source, such as shrinkage or porosity, and those cracks caused by mercury liquid metal embrittlement.

OBJECTS AND SUMMARY OF THE INVENTION

It is an object of the present invention to provide a portable, non-destructive inspection tool for detecting the presence of mercury amalgams on an aluminum surface.

It is a further object of the present invention to provide a method of detecting mercury amalgamation of aluminum prior to the substantial deterioration of the aluminum and before the mercury can penetrate the surface of the aluminum body suspected of contamination.

In accordance with one form of the present invention, a method for detecting mercury amalgamation of an aluminum body includes the steps of contacting a surface of the aluminum body with an electrolyte. Simultaneously with contacting the aluminum body, the electrolyte is also contacted with a reference electrode. The reference electrode is chosen from a metal which is more electropositive than the aluminum body being tested so that the electrolyte creates an electrochemical cell between the aluminum and the reference electrode, which cell produces an electromotive potential between the aluminum and the reference electrode.

The potential difference between the aluminum surface contacted and the reference electrode is then monitored, wherein the magnitude of the potential difference will differ when the aluminum surface contacted with the electrolyte is mercury amalgamated, from when no mercury amalgamation is present in the aluminum surface contacted.

The reference electrode may be saturated calomel, where the calomel is saturated in a potassium chloride solution.

The apparatus for detecting the mercury amalgamation on the aluminum body, in one form of the invention, is an elongated probe. An outer cylindrical wall defines a well for receiving and holding an electrolyte. In communication with the well is a sponge material. The sponge material absorbs and retains the electrolyte, which electrolyte flows from the well into the sponge material.

A reference electrode is also included. The reference electrode is in electrochemical communication with the electrolyte contained in the electrolyte well.

The sponge material has an exposed surface of a predetermined area, which surface is adapted to contact a surface of the aluminum body under investigation. Upon contacting the exposed surface of the sponge material with the surface of the aluminum body, an electrochemical cell between the aluminum body and the reference electrode is created and an electromotive potential difference between the two is produced, the potential difference being different when the aluminum surface contacted with the sponge material is mercury amalgamated from the situation where no mercury amalgamation is present in the aluminum surface.

These and other embodiments, objects, features and advantages of this invention will be apparent from the following detailed description of the illustrative embodiments thereof, which is to be read in connection with the accompanying drawings.

DETAILED DESCRIPTION OF THE PREFERRED EMBODIMENTS

Figure 1:
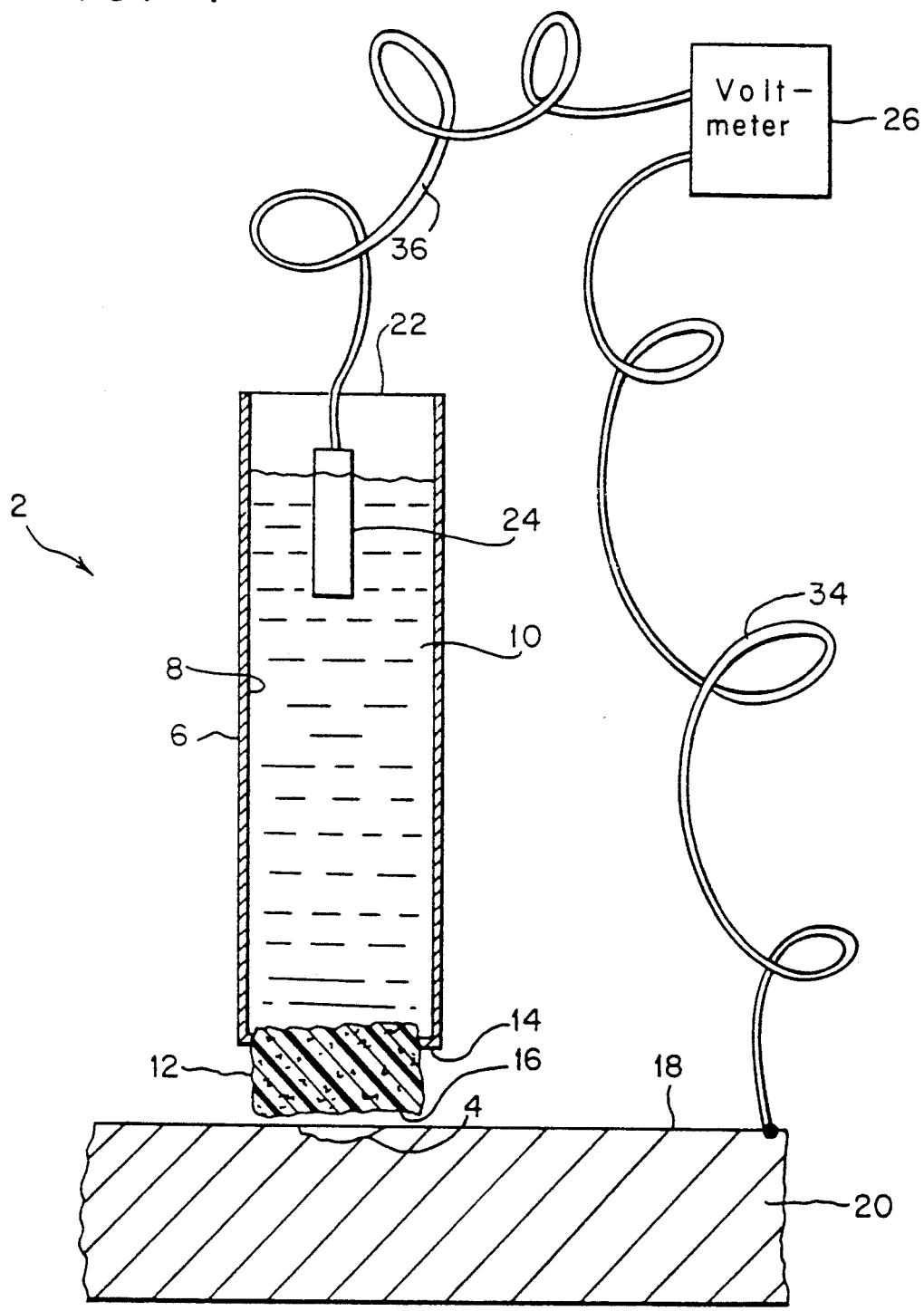
FIG. 1 is a longitudinal cross-sectional view of a probe for detecting mercury amalgamation of an aluminum body, which probe is constructed in accordance with the present invention.

The method of the present invention for detecting mercury amalgamation of an aluminum body basically includes steps which create an electrochemical cell between two dissimilar metals, one of the metals being the aluminum body, and which produces an electromotive potential difference between the aluminum body and the other dissimilar metal.

More specifically, in accordance with the preferred method, a surface of the aluminum body under inspection is contacted with an electrolyte. That electrolyte is simultaneously contacted with a reference electrode.

The reference electrode is preferably formed of a metal which is more electropositive than the aluminum such that the electrolyte creates an electrochemical cell between the aluminum and the reference electrode and produces an electromotive potential difference between the two.

The potential difference between the aluminum surface contacted by the electrolyte and the reference electrode is monitored, such as by a voltmeter.

When mercury amalgamation is present on the surface of the aluminum body, the potential difference between the reference electrode and the body under inspection will be of greater magnitude than when no mercury amalgamation is present in the aluminum surface contacted.

The reference electrode is preferably saturated calomel, and more particularly is calomel saturated in a potassium chloride solution.

The reference electrode and the aluminum body are electrically connected to a voltmeter, which voltmeter is used to measure the potential difference between the two.

When calomel is used as the reference electrode, the potential difference between the aluminum and the calomel reference electrode, when no mercury amalgamation is contacted by the electrolyte, is approximately $-1$ volt. However, when mercury amalgamation is present on the aluminum surface contacted by the electrolyte, the potential difference between the reference electrode and the aluminum body will be approximately 200 millivolts more negative, or $-1.2$ volts.

Accordingly, by contacting the electrolyte over a small but defined area of the surface of the aluminum body and by monitoring the potential difference between the reference electrode and the aluminum body by using the voltmeter, for example, whenever mercury amalgamation is encountered on the aluminum body surface and comes in contact with the electrolyte, the potential difference between the reference electrode and the aluminum body will vary.

The method of the present invention is more accurate in determining whether mercury amalgamation is present on the aluminum surfaces in LNG and LPG refinery equipment than conventional methods, such as by visual observation or through x-ray examination. Also, the method of the present invention is far more sensitive than by detecting cracks using ultrasonic devices, and it can discriminate between cracks filled with mercury and those that are not. In the latter instance, this is an important feature of the invention, because the corrosion potential of the surface of the aluminum body will indicate whether a mercury amalgam is present.

In an alternative form of the invention, a non-amalgamated section of the aluminum body itself may serve as a standard or reference electrode. When the aluminum standard is used, a potential difference of about 200 millivolts or greater will indicate the presence of an amalgam.

Also, it is not necessary for the electrolyte itself to contact the aluminum surface being tested. The well may be divided so that it holds the electrolyte, in contact with the reference electrode, as well as a buffer solution. The buffer solution is in electrochemical communication with the electrolyte and the sponge material, and the buffer solution rather than the electrolyte flows into the sponge material. In this way, no electrolyte will come into contact with the aluminum body, and the buffer solution may be chosen so that it will not harm the aluminum body.

FIG. 1 is a cross-sectional view of a probe 2 which may be used for detecting the presence of a mercury amalgam 4, which probe is constructed in accordance with a preferred form of the present invention. The probe 2 basically includes a hollow cylindrical body 6, which body defines a well 8 in its interior for receiving the electrolyte 10.

A sponge material 12 is mounted on one open end 14 of the cylindrical body 6. The sponge material 12 is in communication with the electrolyte well 8 so that electrolyte 10 may flow into the material and be absorbed by the material and retained thereby. The sponge material 12 extends axially outwardly from the end of the cylindrical body 6, and has an exposed surface 16, which exposed surface is used to contact the surface 18 of the aluminum body 20 under investigation.

The other end 22 of the cylindrical body 6 has a reference electrode 24 mounted on it. The reference electrode 24 is also in communication with the electrolyte 10 filling the well 8 of the probe body. The reference electrode 24 may be an elongated section of metal which is selected to be more electropositive than the aluminum body 20 being tested.

The aluminum body 20 and the reference electrode 24 are connected by leads 34, 36 to a voltmeter 26 or other device which is used to measure the potential difference between the aluminum body and the reference electrode.

When the exposed surface 16 of the sponge material 12 of the probe is placed against the surface 18 of the aluminum body 20 being tested, an electrochemical cell is created between the reference electrode 24 and the aluminum body 20, and a potential difference between the two metals is produced by the cell. If calomel is used as the reference electrode, that potential difference will be approximately $-1$ volt.

When mercury amalgamation is present on the surface of the aluminum body being inspected, as shown at reference numeral 4, and the mercury amalgamation comes in contact with the exposed surface 16 of the sponge material 12 of the probe, the potential difference between the reference electrode 24 and the aluminum body 20, as measured by the voltmeter 26, will drop to $-1.2$ volts. Accordingly, by monitoring the voltmeter 26, the probe may be used to determine the presence or absence of mercury amalgamation on the surface of the aluminum body. The voltage drop of $-1.2$ volts is indicative for the particular example given above.

One of the advantages of the probe 2 is that the electrolyte 10 is maintained in contact with the surface 18 of the aluminum body over a relatively small, well-defined area of the aluminum body. The probe 2 is drawn along the surface 18 of the aluminum body being examined, and because of the small area of the body contacted by the probe, an amalgam 4 on the surface may be pinpointed with accuracy.

Figure 2:
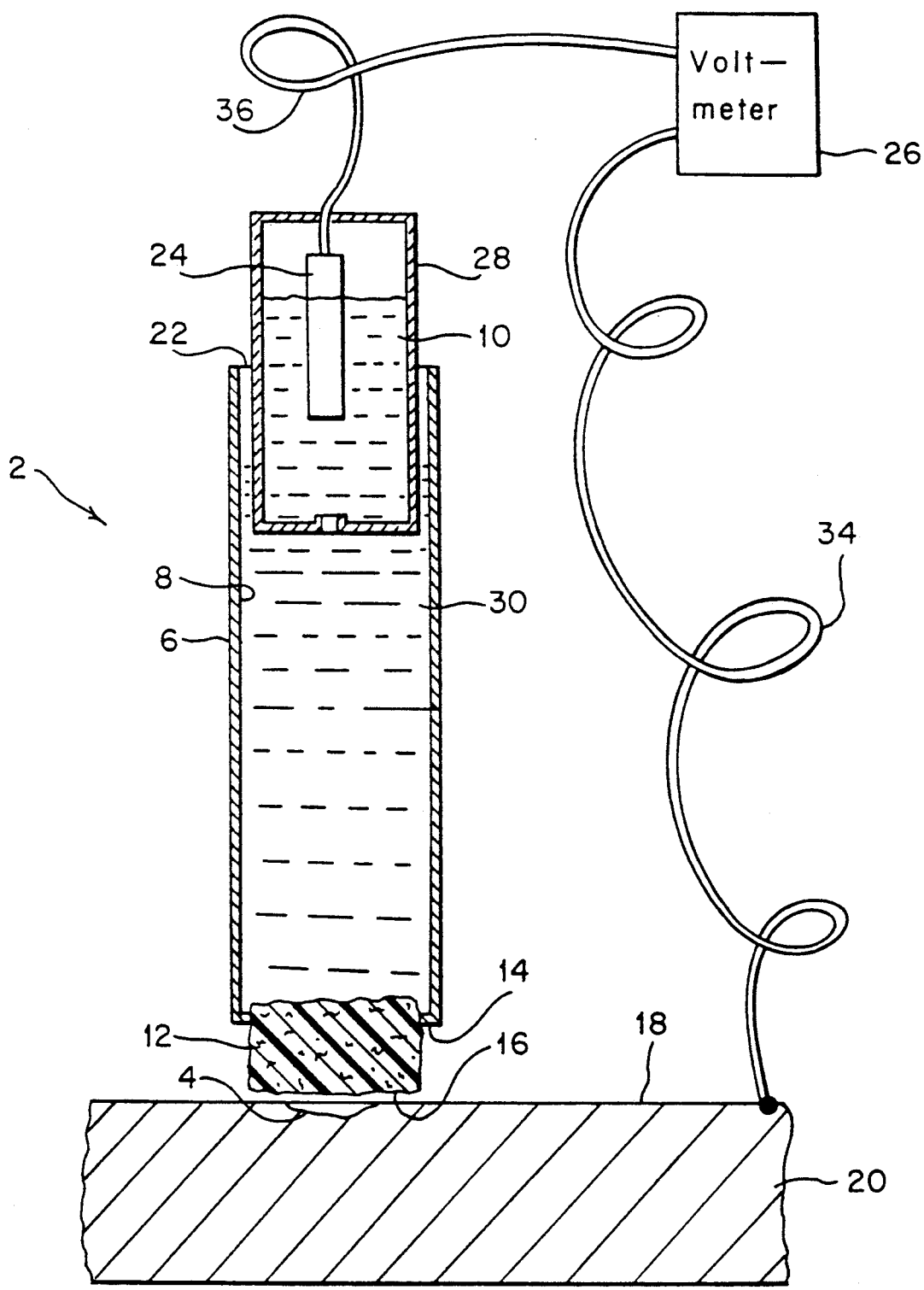
FIG. 2 is a longitudinal cross-sectional view of an alternative form of the probe of the present invention.

In an alternative form of the invention, as shown in FIG. 2, the reference electrode 24 may be housed in a capsule 28 defining a chamber 29 filled with an electrolyte 10, the capsule 28 being at least partially received by the well 8 defined by the cylindrical body. The well 8 is filled with a buffer solution 30 rather than an electrolyte, and the electrolyte 10 and the buffer solution 30 are in communication through a liquid junction or opening 32 formed in the capsule 28. In this embodiment, the sponge material 12 receives the buffer solution 30 so that only the buffer solution comes in contact with the aluminum body 20 being inspected. The buffer solution 30 may be a carbonate or phosphate solution, for example.

The above embodiment has the advantage in that the buffer solution 30 will not cause corrosion to the aluminum body 20, whereas certain electrolyte solutions may cause corrosion. The buffer solution 30 still allows an electrochemical cell to be formed between the aluminum body 20 and the reference electrode 24, and still accurately determines the presence of a mercury amalgam 4 on the surface of the aluminum body.

The apparatus of the present invention has the ability of controlling the surface area of the aluminum body surveyed by using a suitably sized probe tip (i.e., the exposed surface of the sponge material). The probe can easily be drawn across the surface of the aluminum body to accurately pinpoint a mercury amalgam on the surface.

Although the illustrative embodiments of the present invention have been described herein with references to the accompanying drawing, it is to be understood that the invention is not limited to those precise embodiments, and that various other changes and modifications may be effected therein by one skilled in the art without departing from the scope or spirit of the invention.

What is claimed is:

1. A method for detecting mercury amalgamation of an aluminum body, which comprises the steps of:
   (a) contacting a surface of the aluminum body with an electrolyte, the electrolyte being contained in means defining a well, the well defining means being in communication with an electrolyte absorbing member, the electrolyte from the well defining means being absorbed by the absorbing member, the absorbing member and the electrolyte absorbed thereby being in contact with the aluminum body surface;
   (b) simultaneously with step (a) at least electrically coupling the electrolyte to a reference electrode, the reference electrode being formed of a metal which is more electropositive than the aluminum body, such that the electrolyte creates an electrochemical cell between the aluminum body and the reference electrode, which cell produces an electromotive potential difference between the aluminum and the reference electrode; and
   (c) monitoring the potential difference between the aluminum surface contacted and the reference electrode, wherein the potential difference will deviate when the aluminum surface contacted with the electrolyte is mercury amalgamated from when no mercury amalgamation is present in the contacted aluminum surface.

2. A method as defined by claim 1, wherein the reference electrode is saturated calomel.

3. A method as defined by claim 1, wherein the reference electrode is calomel and is saturated in a potassium chloride solution.

4. A method as defined by claim 1, wherein the reference electrode is a surface portion of the aluminum body having no mercury amalgamation present therein.

5. A method for detecting mercury amalgamation of an aluminum body, which comprises the steps of:
   contacting a surface of the aluminum body with a buffer solution, the buffer solution being contained in means defining a well, the well defining means being in communication with a buffer solution absorbing member, the buffer solution from the well defining means being absorbed by the absorbing member, the absorbing member and the buffer solution absorbed thereby being in contact with the aluminum body surface;
   contacting the buffer solution with an electrolyte, the electrolyte being contained in means defining a chamber, the chamber being in communication with the well;
   at least electrically coupling the electrolyte to a reference electrode, the reference electrode being formed of a metal which is more electropositive than the aluminum body, such that the electrolyte creates an electrochemical cell between the aluminum and the reference electrode, which ell produces an electromotive potential between the aluminum and the reference electrode; and
   monitoring the potential difference between the aluminum surface contacted and the reference electrode, wherein the potential difference will deviate when the aluminum surface contacted with the buffer solution is mercury amalgamated from when no mercury amalgamation is present in the contacted aluminum surface.

* * * * *